(12) United States Patent
Eil

(10) Patent No.: US 11,202,564 B2
(45) Date of Patent: Dec. 21, 2021

(54) INFORMATION DISPLAY FOR PATIENT

(71) Applicant: Alcon Inc., Fribourg (CH)

(72) Inventor: Martin Eil, Berlin (DE)

(73) Assignee: Alcon Inc., Fribourg (CH)

(*) Notice: Subject to any disclaimer, the term of this patent is extended or adjusted under 35 U.S.C. 154(b) by 308 days.

(21) Appl. No.: 16/380,189

(22) Filed: Apr. 10, 2019

(65) Prior Publication Data

US 2019/0313893 A1 Oct. 17, 2019

Related U.S. Application Data

(60) Provisional application No. 62/656,052, filed on Apr. 11, 2018.

(51) Int. Cl.
| | |
|---|---|
| *A61B 3/00* | (2006.01) |
| *G09B 5/02* | (2006.01) |
| *G09B 5/04* | (2006.01) |
| *G09B 23/28* | (2006.01) |
| *G09B 5/06* | (2006.01) |

(52) U.S. Cl.
CPC .......... *A61B 3/0041* (2013.01); *A61B 3/0083* (2013.01); *G09B 5/02* (2013.01); *G09B 5/06* (2013.01); *G09B 23/286* (2013.01)

(58) Field of Classification Search
CPC ..... A61B 3/0083; A61B 3/145; A61B 3/0041; A61B 3/10; A61B 3/14; A61B 3/15; A61B 3/18; G09B 5/02; G09B 5/06; G09B 5/065; G09B 5/067
See application file for complete search history.

(56) References Cited

U.S. PATENT DOCUMENTS

| | | | | |
|---|---|---|---|---|
| 6,108,634 | A | * | 8/2000 | Podnar .................... A61B 3/18 705/2 |
| 2005/0225720 | A1 | * | 10/2005 | Ridings ................. A61B 3/032 351/200 |
| 2011/0238431 | A1 | | 9/2011 | Cionni et al. |
| 2011/0242306 | A1 | * | 10/2011 | Bressler .................. A61B 3/12 348/78 |
| 2012/0075586 | A1 | | 3/2012 | Kirschen et al. |
| 2018/0070820 | A1 | * | 3/2018 | Fried ....................... A61B 3/18 |
| 2018/0286509 | A1 | * | 10/2018 | Shah ..................... G09B 5/065 |
| 2019/0082951 | A1 | * | 3/2019 | Merriam .............. A61B 3/0033 |
| 2019/0150727 | A1 | * | 5/2019 | Blaha ................... A61B 3/0025 |
| 2019/0209070 | A1 | * | 7/2019 | Cherchi ................ A61B 3/113 |

\* cited by examiner

*Primary Examiner* — Jordan M Schwartz

(57) ABSTRACT

Implementation of a patient display in ophthalmic procedures, such as diagnostics and surgery, is disclosed herein. In an exemplary aspect, the present disclosure may be directed to an ophthalmic system. The ophthalmic system may include a patient display, a medical device, a memory, and a processor. The memory may be configured to store one or more video files that include information for a patient relating to the medical device. The processor may be configured to execute instructions to perform the following steps: receive input from an operator of a selection of at least one of the one or more video files; and display the selected at least one of the one or more video files on the patient display.

18 Claims, 4 Drawing Sheets

INFORMATION DISPLAY FOR PATIENT

BACKGROUND

During standard ophthalmic diagnostics and surgery workflow, the patient may come into the clinic for diagnostics before the surgery. The diagnostics may be used to obtain measurements for the diagnosis of eye problems, which may be corrected with a subsequent surgical procedure. The diagnostics may also be used to obtain measurements needed for the subsequent surgical procedure. The diagnostics may also not be connected with a surgical procedure, but rather may be used to monitor or diagnosis eye problems that a patient may be experiencing. The diagnostics may include a number of measurements, including, but not limited to, measurement of refraction, axial length of the eye, intraocular pressure, and/or screening of the background of the eye.

The patient typically has very little information about the diagnostics. For example, the patient may not know what kind of measurements are going to be taken, what happens before and after the measurements, or what is going to happen during the subsequent surgical procedure. Due to the lack of information, the patient may experience anxiety both before and during the measurements. The anxiety may also be increased, for example, due to the patient waiting for the clinical operator in the room where the measurement may be performed. However, due to the anxiety of the patient, the measurements may be less accurate than if the patient was relaxed and calm. This negative impact on the measurements may be due to a number of reasons, including the impact of anxiety on the eyes. For example, anxiety may cause dilation of the pupils and tightening of facial muscles, which can impact vision, as well as result in eye pain. In addition, due to anxiety and/or incomplete instructions, the measurement may also be inaccurate. For example, the patient may not properly fixate on the target and/or may not follow instructions from the clinical operator.

SUMMARY

In an exemplary aspect, the present disclosure may be directed to an ophthalmic system. The ophthalmic system may include a patient display, a medical device, a memory, and a processor. The memory may be configured to store one or more video files that include information for a patient relating to the medical device. The processor may be configured to execute instructions to perform the following steps: receive input from an operator of a selection of at least one of the one or more video files; and display the selected at least one of the one or more video files on the patient display.

In another exemplary aspect, the present disclosure may be directed to a method for conducting an ophthalmic procedure. The method may include selecting at least one video to display to a patient on a patient display, wherein the video may include information relating to a medical device used in the ophthalmic procedure. The method may further include displaying the at least one video to the patient on the patient display. The method may further include performing the ophthalmic procedure.

The different aspects may include one or more of the following features. The processor may be communicatively coupled to the patient display and the medical device. The ophthalmic system may further include a table that supports at least one of the patient display or the medical device. The ophthalmic system may further include an operator display configured to display information to the operator. The ophthalmic system may further include a table, wherein the patient display is coupled to the table, and wherein the operator display is coupled to the table. The patient display may be positioned in a patient station, wherein the operator display may be positioned in an operator station, and wherein the patient station and the operator station may be disposed on opposite sides of the table. The information in the one or more video files may include instructions for the patient. The instructions may include an instruction for the patient to position a body part in a fixation device. The medical device may include a device configured to obtain at least one measurement of an eye of the patient. The memory may be remote from the patient display, such that video from the video is streamed over a network. The video files may be digital video files stored in a compressed format. The ophthalmic system may further include: a table that supports the medical device, wherein the medical device includes an ophthalmic measurement device; an operator display communicatively coupled to the processor; wherein the information on the one or more video files includes instructions for the patient relating to the medical device. The processor may be communicatively coupled to the medical device. The ophthalmic system may further include an input device configured to receive input from the operator. The ophthalmic procedure may be initiated on the medical device, wherein the initiating includes receiving a command from an operator. An operator may be positioned on an opposite side of a table from the patient, wherein the patient display and a medical device may be supported by the table. The step of performing the ophthalmic procedure may include obtaining one or more ophthalmic measurements.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

DETAILED DESCRIPTION

Figure 1:
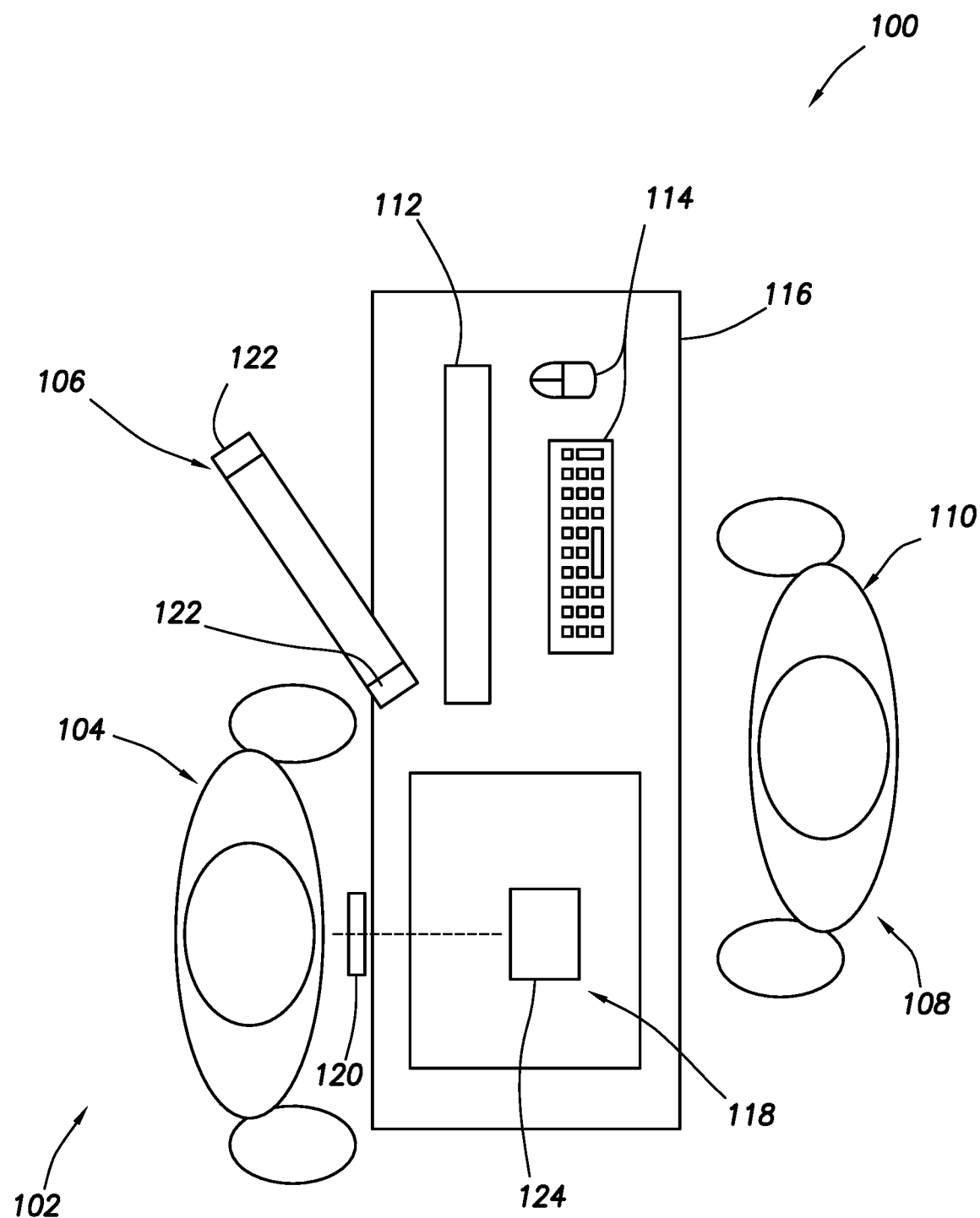
FIG. 1 is a schematic illustration of an ophthalmic system in accordance with embodiments of the present disclosure.

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

Embodiments may generally relate to ophthalmic procedures. More particularly, embodiments may generally relate to implementation of a patient display in ophthalmic procedures, such as diagnostics and surgery. The patient display may be secured to the medical device and be visible to the patient. On the patient display, a video may be displayed to the patient that contains instructions and/or other information about the upcoming ophthalmic procedure. The video may be displayed, for example, while the clinical operator is preparing for the ophthalmic procedure or the patient is waiting for the clinical operator. Among other benefits, the video may save valuable time for the clinical operator as the video can provide the patient with information that would typically be provided by the clinical operator. In addition, the video may reduce patient anxiety by providing the patient with information about the procedure, which may lead to a better measurement. In addition, by providing information to the patient, the procedure may be standardized, for example, reducing the tendency for human error.

The patient display may be used to provide information to a patient in connection with any suitable ophthalmic procedure. Suitable ophthalmic procedures may include, but are not limited to, diagnostics and surgery. The ophthalmic diagnostics may include obtaining measurements for the diagnosis, treatment, and/or monitoring of eye problems that the patient may be experiencing. In some embodiments, the ophthalmic diagnostics may include obtaining measurements for a subsequent ophthalmic surgery. The ophthalmic diagnostics may include a number of measurements, including, but not limited to, measurement of refraction, axial length of the eye, intraocular pressure, and/or screening of the background of the eye. The ophthalmic surgery may include any a variety of surgical procedures that may be performed on the human eye, including, but not limited to, cataract surgery, glaucoma surgery, corneal refraction surgery, refractive surgery, and vitreo-retinal surgery.

FIG. 1 illustrates an example ophthalmic system 100 in accordance with embodiments of the present disclosure. As illustrated, the ophthalmic system 100 may include a patient station 102 for placement of a patient 104. In the illustrated embodiment, the patient station 102 may also include a patient display 106 for providing information to the patient 104. The ophthalmic system 100 may also include an operator station 108 in which a clinical operator 110 may be positioned. The operator station 108 may also include an operator display 112 for providing information to the clinical operator 110 and one or more input devices 114. The ophthalmic system 100 may also include a table 116 to which the patient display 106 and/or the operator display 112 may be coupled. The ophthalmic system 100 may also include a medical device 118 that may be used in the diagnosis and/or treatment of the patient 104.

The patient station 102 may be any suitable station for positioning of the patient 104 for an ophthalmic procedure. In the illustrated embodiment, the patient station 102 may include a fixation device 120. The fixation device 120 may be any suitable device for maintaining the patient 104 a fixed distance from the medical device 118. Suitable examples of the fixation device 120 may include, but are not limited to, a chin rest or a forehead rest. While not illustrated, the patient station 102 may also include a patient support, such as a chair, platform, examination table, or bed, for supporting the patient 104 during the ophthalmic procedure. The clinical operator 110 may direct the patient 104 to position themselves on the patient support and, at the desired time, to position their body in the fixation device 120.

The patient display 106 may also be positioned in the patient station 102. In the illustrated embodiment, the patient display 106 may be supported by the table 116. In some embodiments, the patient display 106 may be supported on the table 116, for example, using a monitor stand (not shown). In other embodiments, the patient display 106 may be coupled to the table 116. Any suitable technique may be used to couple the patient display 106 to the table 116, including, but not limited to, mechanical fasteners, such as bolts and/or clamps. In some embodiments, the patient display 106 may be a tablet or other portable device. In some embodiments, the patient display 106 may be a touch screen operable to receive patient input. For example, the patient 104 may confirm that the patient 104 understands what is going to happen or indicate that there may be additional questions. The patient station 102 may also include one or more speakers 122. In the illustrated embodiment, the speakers 122 may be coupled to the patient display 106. However, it is not necessary for the speakers 122 to be coupled to the patient display 106, but the speakers 122 may be otherwise positioned as desired for a particular application. For example, the speakers 122 may be disposed on the table 116 or free standing.

The patient display 106 may be used to provide information to the patient 104. By way of example, the patient display 106 may display a video to the patient 104. The speakers 122 may emit sound associated with the video. The video may provide instructions and/or other information relating to the medical device 118 about the upcoming ophthalmic procedure. By way of example, the video may inform the patient 104 about the upcoming process and procedures for the ophthalmic procedure. By way of further example, the video may provide instructions to the patient 104. In some embodiments, the instructions may include requesting the patient to engage the fixation device 120, for example, requesting the patient to place a specified body part, such as a chin or forehead, into the fixation device 120. As previously described, the patient 104 may have to wait in the patient station 102 for a period of time (e.g., 5 minutes, 10 minutes, or even longer). By providing information and/or instructions to the patient 104 during this period, the anxiety of the patient 104 may be reduced, potentially leading to an improved ophthalmic procedure. For example, reduction in anxiety may lead to more accurate measurements.

The operator station 108 may be any suitable station for positioning of the clinical operator 110 for an ophthalmic procedure. The operator station 108 may enable the clinical operator 110 to observe and/or control the ophthalmic procedure. The clinical operator 110 may include any suitable operator of the patient display 106 and/or the medical device 118, including, but not limited to, a physician, a technician, or other suitable personal that may perform the ophthalmic procedure and/or assist with the ophthalmic procedure. The operator station 108 may include an operator display 112 and one or more input devices 114. In some embodiments, the operator display 112 may display a control panel that includes information concerning the ophthalmic procedure.

By way of example, the operator display 112 may include information concerning the video displayed to the patient 104. The one or more input devices 114 may include any suitable device for inputting information, including, but not limited to, a keyboard and a mouse. In some embodiments (not shown), the one or more input devices 114 may be integrated into the operator display 112 in the form of a touch screen. Using the one or more input devices 114 and the operator display 112, the clinical operator 110 may be able to input information concerning the patient 104, for example, by way of a graphical user interface. In addition, using the one or more input devices 114 and the operator display 112, the clinical operator 110 may also be able to control the patient display 106 and/or the medical device 118. For example, the clinical operator 110 may be able to initiate display of the video on the patient display 106. By way of further example, the clinical operator 110 may be able to start and/or stop the measurement and/or procedure implemented via the medical device 118. The clinical operator may also be able to implement a vision testing sequence using the operator display 112 and the one or more input devices 114. In this manner, the clinical operator 110 may be able to monitor and/or control the ophthalmic procedure and associated operation of the medical device 118.

In the illustrated embodiment, the operator display 112 may be supported by the table 116. In some embodiments, the operator display 112 may be supported on the table 116, for example, using a monitor stand (not shown). In other embodiments, the operator display 112 may be coupled to the table 116. Any suitable technique may be used to couple the operator display 112 to the table 116, including, but not limited to, mechanical fasteners, such as bolts, and/or clamps. In the illustrated embodiment, the operator station 108 is shown on an opposite side of the table 116 from the patient station 102. However, the operator station 108 is not required to be positioned in this manner, but may be positioned on the same side or an adjacent side of the table 116 from the patient station 102 as desired for a particular application.

The ophthalmic system 100 may also include a medical device 118. The medical device 118 may be used in the diagnosis and/or treatment of the patient 104. Suitable examples of the medical device 118 may include, but are not limited to, devices for the measurement of refraction, axial length of the eye, intraocular pressure of the eye, and/or screening of the background of the eye. the illustrated embodiment, the medical device 118 may be supported by the table 116. In some embodiments, the medical device 118 may be supported on the table 116, for example, using a stand (not shown). In other embodiments, the medical device 118 may be coupled to the table 116. Any suitable technique may be used to couple the medical device 118 to the table 116, including, but not limited to, mechanical fasteners, such as bolts and/or clamps. In some embodiments, the medical device 118 may further include a clinical display 124 or other suitable device, such as a camera, sensor, or any combination of these devices. Suitable sensors may include, but are not limited to, wavefront sensors and light detectors for optical coherence tomography.

Figure 2:
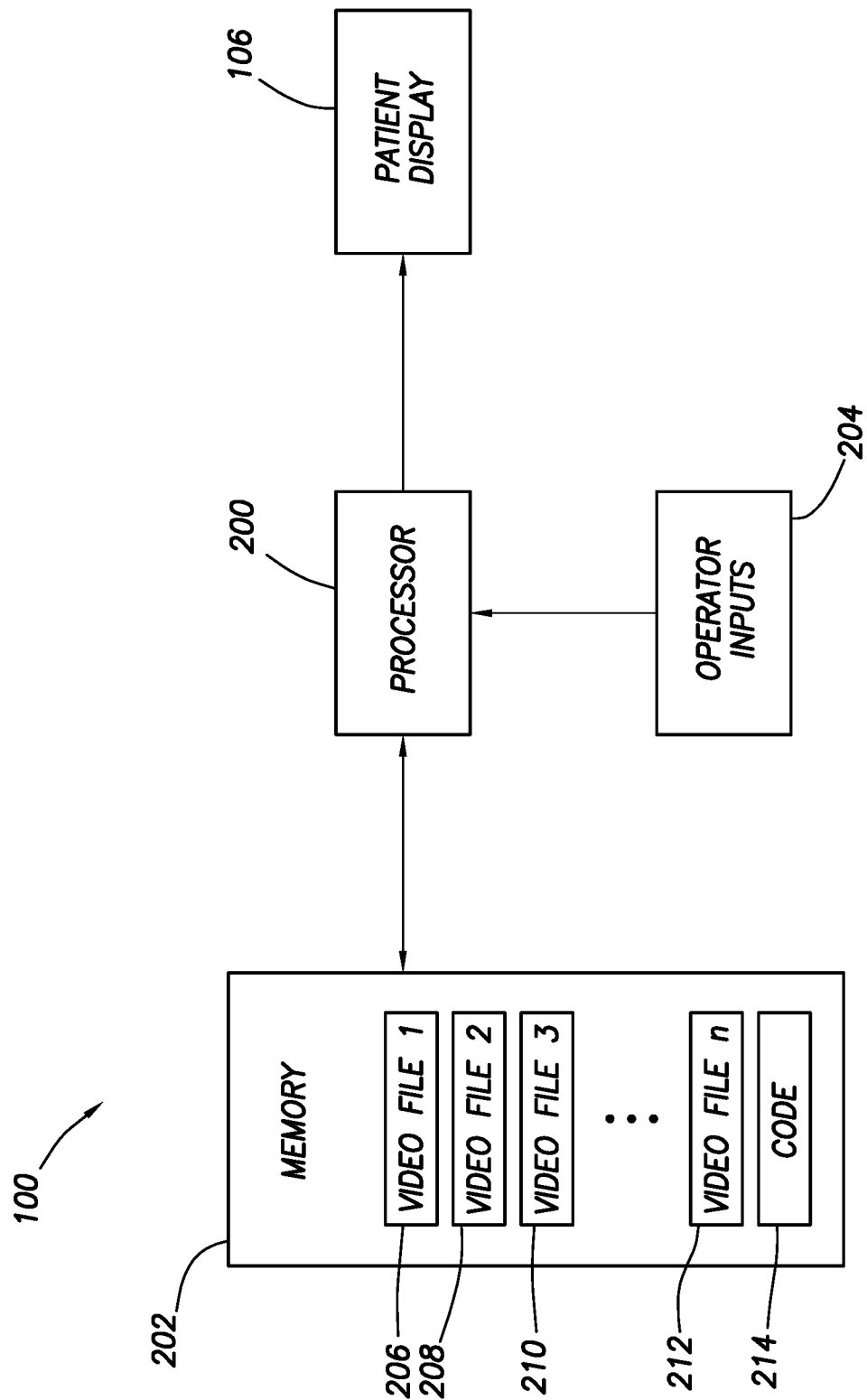
FIG. 2 is a block diagram of certain components of an ophthalmic system in accordance with embodiments of the present disclosure.

FIG. 2 is a block diagram of certain components of the ophthalmic system 100 in accordance with embodiments of the present disclosure. As illustrated, the ophthalmic system 100 may include a patient display 106, a processor 200, and a memory 202. The processor 200 may include any suitable device for processing instructions, including, but not limited to, a microprocessor, microcontroller, embedded microcontroller, programmable digital signal processor, or other programmable device. The processor 200 may also, or instead, be embodied in an application specific integrated circuit, a programmable gate array, programmable array logic, or any other device or combinations of devices operable to process electric signals. The processor 200 may be communicatively coupled to the patient display 106. The connection between the processor 200 and the patient display 106 may be a wired connection or a wireless connection, as desired for a particular application. The processor 200 can be configured to receive operator inputs 204, for example, to start the display of the video and/or to stop the display of the video.

The ophthalmic system 100 may also include memory 202, which may be internal or external, for example. The memory 202 may include any suitable form of data storage, including, but not limited to, electronic, magnetic, or optical memory, whether volatile or non-volatile. The memory 202 may include one or more video files 206, 208, 210, 212 and code 214. The one or more video files 206, 208, 210, 212 may be in any suitable format for storing digital video, including, but not limited to, .flv, .m4v, .giv, .wmv, .mov, or .mpg. The one or more video files 206, 208, 210, 212 may be in compressed format or uncompressed format as desired for a particular application. While the one or more video files 206, 208, 210, 212 are shown stored in memory 202, it should be understood that the video displayed on the patient display 106 may also be streamed from video stored remote from the patient display 106. For example, the video may be stored remote from the patient display 106 and streamed in a compressed formate over a network, such as the Internet. The one or more video files 206, 208, 210, 212 may contain digital video. The digital video stored on the one or more video files 206, 208, 210, 212 may contain the information and/or instructions for the patient 104. The one or more video files 206, 208, 210, 212 may each contain different information for the patient 104. The operator inputs 204 may include a selection of a particular one of the one or more video files 206, 208, 210, 212 for display on the patient display 106. While the preceding description describes the use of digital video, embodiments may also incorporate other video recording techniques such as tapes.

The code 214 stored on the memory 202 may include instructions that may be executable by the processor 200. The instructions may include instructions for the processor 200 to access the video files 206, 208, 210, 212 in response to operator inputs 204. The code 214 may be created, for example, using any suitable programming language, including but not limited to, C++ or any other programming language (including assembly languages, hardware description languages, and database programming languages) that may be stored, compiled, or interpreted to be executable by the processor 200.

In operation, operator inputs 204 may be provided to the processor 200. The operator inputs 204 may include, for example, a command to begin a video. The processor 200 may then access the memory 202, which includes the one or more video files 206, 208, 210, 212 that include the information and/or instructions on the ophthalmic procedure for the patient 104 (e.g., shown on FIG. 1). The processor 200 can read the one or more video files 206, 208, 210, 212 and display the associated video from the one or more video files 206, 208, 210, 212 on the patient display 106.

Figure 3:
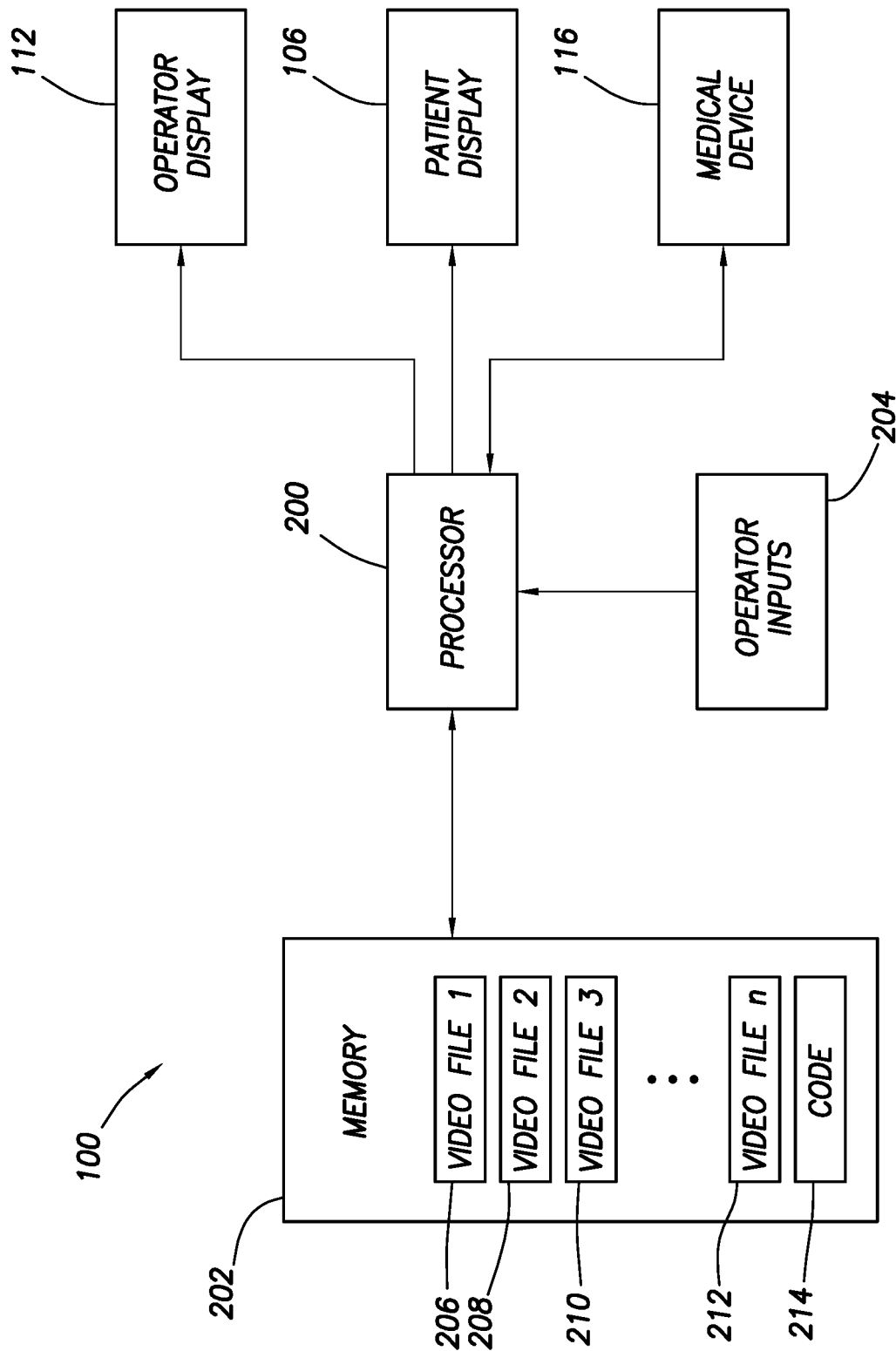
FIG. 3 is a block diagram of certain components of an ophthalmic system in accordance with embodiments of the present disclosure.

FIG. 3 is a block diagram of certain components of the ophthalmic system 100 in accordance with embodiments of the present disclosure. As illustrated, the ophthalmic system 100 may include a patient display 106, a processor 200, and memory 202. In the illustrated embodiment, the operator display 112 and the medical device 118 may also be communicatively coupled to the processor 200. The connection between the processor 200 and the operator display 112 may be a wired connection or a wireless connection, as desired for a particular application. The connection between the processor 200 and the medical device 118 may be a wired connection or a wireless connection, as desired for a particular application. The processor 200 can be configured to receive operator inputs 204, for example, to start the display of the video and/or to stop the display of the video on the patient display 106. The processor may also be configured to display a graphical user interface on the operator display 112. The graphical user interface on the operator display 112 may enable the operator to control the display of video on the patient display 106, input information associated with the patient 104 (e.g., shown on FIG. 1), and/or control the medical device 118. By way of example, the operator inputs 204 may include a command to initiate the ophthalmic procedure. The operator inputs 204 may also include one or more parameters associated with measurements taken during the ophthalmic procedure. The code 214 stored on the memory 202 may also include the application for operation of the medical device 118.

Figure 4:
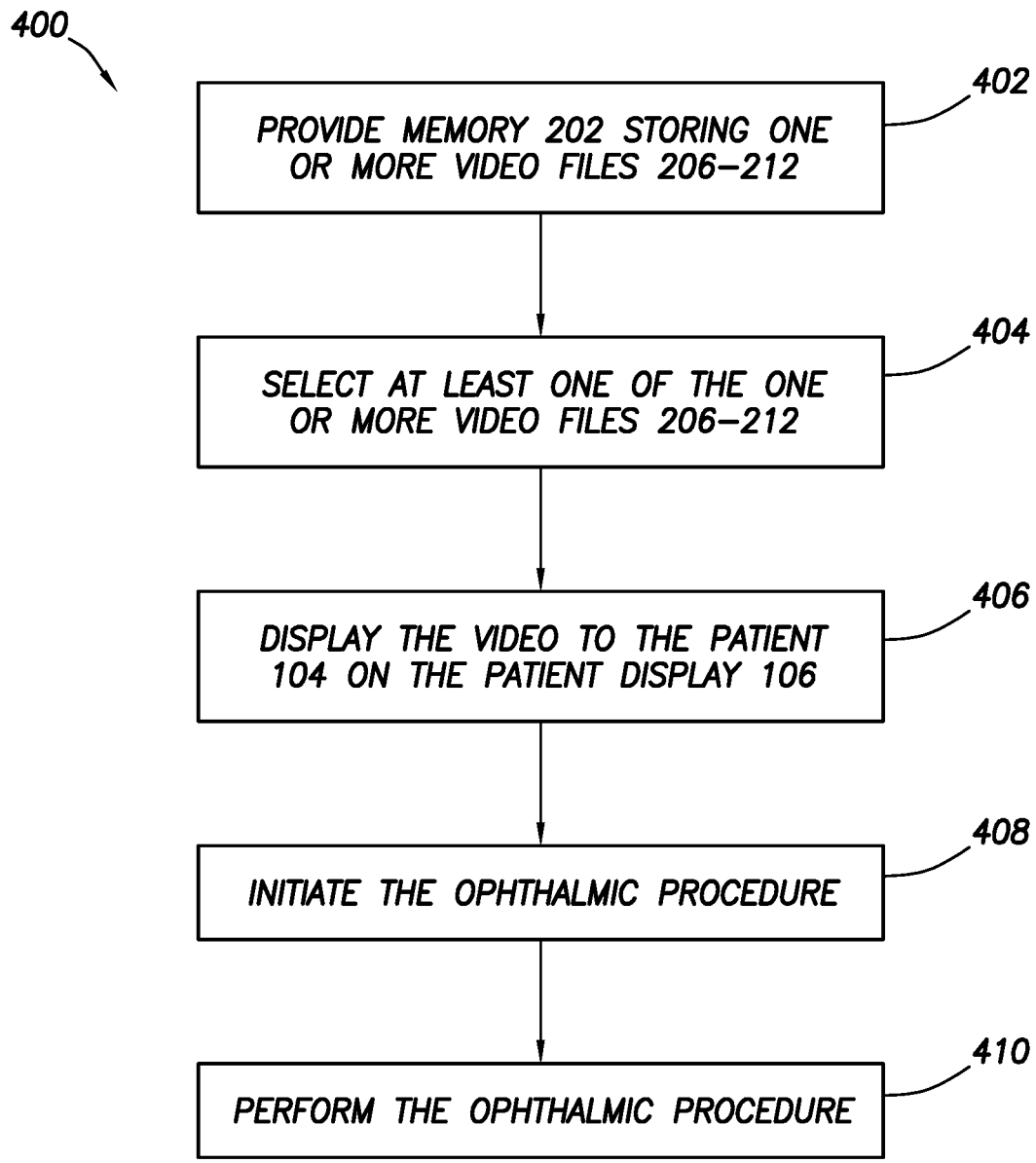
FIG. 4 is a flow chart illustrating an example method for implementing a patient display into an ophthalmic procedure.

FIG. 4 is a flowchart of an example method 400 for displaying information according to embodiments of the present invention. At block 402, the memory 202 may be provided storing one or more video files 206, 208, 210, 212. At block 404, at least one of the one or more video files 206, 208, 210, 212 may be selected. For example, the clinical operator 110 (e.g., shown on FIG. 1) may select at least one of the one or more of the video files 206, 208, 210, 212 for the video. At block 406, the video may be displayed to the patient 104 on the patient display 106. The video may be displayed from at least one of the one or more video files 206, 208, 210, 212. The video may include instructions and/or information relating to the ophthalmic procedure. At block 408, the ophthalmic procedure may be initiated. The ophthalmic procedure may be initiated, for example, by the clinical operator 110. At block 410, the ophthalmic procedure may be performed. Performing the ophthalmic procedure may include obtaining one or more measurements of the eye of the patient 104.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. An ophthalmic system comprising:
   a patient display;
   a medical device configured for obtaining, during a diagnostic workflow, a plurality of different diagnostic measurements of a patient's eye for a subsequent surgical procedure;
   a memory configured to store one or more video files that comprise information for a patient relating to each of:
      the medical device,
      the kind of measurements which are going to be taken during the diagnostic workflow,
      information related to what happens before the measurements are taken during the diagnostic workflow,
      information related to what happens during the taking of the measurements that are taken during the diagnostic workflow, and
      what is going to happen during the subsequent surgical procedure; and
   a processor configured to execute instructions to perform the following steps:
      receive input from an operator of a selection of at least one of the one or more video files; and
      display the selected at least one of the one or more video files on the patient display.

2. The ophthalmic system of claim 1, wherein the processor is communicatively coupled to the patient display and the medical device.

3. The ophthalmic system of claim 1, further comprising a table that supports at least one of the patient display or the medical device.

4. The ophthalmic system of claim 1, further comprising an operator display configured to display information to the operator.

5. The ophthalmic system of claim 4, further comprising a table, wherein the patient display is coupled to the table, and wherein the operator display is coupled to the table.

6. The ophthalmic system of claim 5, wherein the patient display is positioned in a patient station, wherein the operator display is positioned in an operator station, and wherein the patient station and the operator station are disposed on opposite sides of the table.

7. The ophthalmic system of claim 1, wherein the information in the one or more video files comprises instructions for the patient.

8. The ophthalmic system of claim 7, wherein the instructions comprise an instruction for the patient to position a body part in a fixation device.

9. The ophthalmic system of claim 1, wherein the memory is remote from the patient display, such that video from the video is streamed over a network.

10. The ophthalmic system of claim 1, wherein the video files are digital video files stored in a compressed format.

11. The ophthalmic system of claim 1, further comprising:
    a table that supports the medical device, wherein the medical device comprises an ophthalmic measurement device;
    an operator display communicatively coupled to the processor; and
    wherein the information on the one or more video files comprises instructions for the patient relating to the medical device.

12. The ophthalmic system of claim 11, wherein the processor is communicatively coupled to the medical device.

13. The ophthalmic system of claim 1, further comprising an input device configured to receive input from the operator.

14. A method for conducting an ophthalmic procedure, comprising:
    selecting a plurality of videos to display to a patient on a patient display, wherein the videos comprise information relating to a medical device used in the ophthalmic procedure, the medical device configured for obtaining, during a diagnostic workflow, a plurality of different diagnostic measurements of a patient's eye for a subsequent surgical procedure;
    displaying the plurality of videos to the patient on the patient display, wherein the plurality of videos include at least a video describing each of:
       the medical device,
       the kind of measurements which are going to be taken during the diagnostic workflow,
       information related to what happens before the measurements are taken during the diagnostic workflow, information related to what happens during the taking of the measurements that are taken during the diagnostic workflow, and what is going to happen during the subsequent surgical procedure; and performing the ophthalmic procedure.

15. The method of claim 14, further comprising initiating the ophthalmic procedure on the medical device, wherein the initiating comprises receiving a command from an operator.

16. The method of claim 14, wherein the information comprises instructions for the patient.

17. The method of claim 16, wherein the information comprises an instruction for the patient to position at least one body part in a fixation device.

18. The method claim 14, wherein an operator is positioned on an opposite side of a table from the patient, wherein the patient display and the medical device are supported by the table.

* * * * *